(12) United States Patent
McKernan

(10) Patent No.: US 8,966,781 B1
(45) Date of Patent: Mar. 3, 2015

(54) SPORTS EQUIPMENT SANITIZER SYSTEM

(71) Applicant: Bruce McKernan, Woodhaven, NY (US)

(72) Inventor: Bruce McKernan, Woodhaven, NY (US)

(73) Assignee: Gina McKernan, Woodhaven, NY (US)

( * ) Notice: Subject to any disclaimer, the term of this patent is extended or adjusted under 35 U.S.C. 154(b) by 172 days.

(21) Appl. No.: 13/851,431

(22) Filed: Mar. 27, 2013

Related U.S. Application Data

(60) Provisional application No. 61/693,958, filed on Aug. 28, 2012.

(51) Int. Cl.
*F26B 5/06* (2006.01)
*A61L 2/16* (2006.01)

(52) U.S. Cl.
CPC . *A61L 2/16* (2013.01); *Y10S 68/903* (2013.01)
USPC ............... 34/105; 34/289; 34/381; 211/85.7; 211/189; D32/59; 223/73; 422/292; 38/1 A; 68/903

(58) Field of Classification Search
USPC ............. 34/90, 104, 105, 103, 289, 380, 381; 211/85.7, 182, 189; D32/58, 59; 223/70, 73; 422/5, 292; 38/14, 1 A; 68/5 D, 903
See application file for complete search history.

(56) References Cited

U.S. PATENT DOCUMENTS

| | | | |
|---|---|---|---|
| 3,568,900 A * | 3/1971 | Paris ............................... | 223/70 |
| 3,739,496 A * | 6/1973 | Buckley et al. ................ | 34/210 |
| 4,173,300 A * | 11/1979 | Sanko .............................. | 223/70 |
| 4,493,160 A * | 1/1985 | Brembilla et al. ................ | 38/14 |
| 4,625,432 A * | 12/1986 | Baltes ............................. | 34/621 |
| 5,377,849 A * | 1/1995 | Martin ......................... | 211/85.7 |
| 5,412,928 A * | 5/1995 | Reithel ......................... | 34/104 |
| 5,592,750 A * | 1/1997 | Eichten ......................... | 34/104 |
| D394,926 S * | 6/1998 | Lindsay ........................ | D32/58 |
| 5,862,606 A * | 1/1999 | Jannach ......................... | 34/106 |
| 6,845,569 B1* | 1/2005 | Kim .............................. | 34/106 |
| 6,880,711 B2* | 4/2005 | Collier ........................ | 211/85.7 |
| 6,889,449 B2 | 5/2005 | Silver | |
| 7,103,989 B2 | 9/2006 | Rosseau et al. | |
| 7,430,816 B1* | 10/2008 | Lozenski ........................ | 34/104 |
| 7,467,481 B2* | 12/2008 | Christian ........................ | 34/104 |
| D616,621 S * | 5/2010 | Prokop ......................... | D32/58 |
| 7,984,567 B2* | 7/2011 | Bertakis ........................... | 34/97 |
| 8,393,482 B2* | 3/2013 | Durham ...................... | 211/85.7 |
| 2005/0193585 A1* | 9/2005 | Silver ............................ | 34/201 |
| 2005/0204579 A1* | 9/2005 | Rosseau et al. ................. | 34/104 |
| 2007/0086914 A1 | 4/2007 | Antinozzi | |

* cited by examiner

*Primary Examiner* — Steve M Gravini

(57) ABSTRACT

An equipment rack system includes a plurality of holders at least including a pair of first holders, a pair of second holders, a pair of third holders, a pair of fourth holders, and a pair of fifth holders, a base; a vertical column have a first end and a second end; a valve; and a powerer. Each pair of first holders, the pair of second holders, the pair of third holders, the pair of fourth holders, and the pair of fifth holders comprise fluid apertures about their lengths. The equipment is placed on the pair of first holders, the pair of second holders, the pair of third holders, the pair of fourth holders, and the pair of fifth holders on the equipment rack during an in-use condition to sanitize and air dry equipment to neutralize odors, and eliminate bacteria, and germs.

20 Claims, 5 Drawing Sheets

SPORTS EQUIPMENT SANITIZER SYSTEM

CROSS-REFERENCE TO RELATED APPLICATION

The present application is related to and claims priority from prior provisional application Ser. No. 61/693,958, filed Aug. 28, 2012 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

The following includes information that may be useful in understanding the present invention(s). It is not an admission that any of the information provided herein is prior art, or material, to the presently described or claimed inventions, or that any publication or document that is specifically or implicitly referenced is prior art.

BACKGROUND OF THE INVENTION

1. Field of the Invention

The present invention relates generally to the field of sanitizing devices and more specifically relates to a sports equipment sanitizer.

2. Description of the Related Art

Perspiration is a fact of life. In simple terms, perspiration is the evaporation of sweat through thousands of glands located all over the body. Serving to control body temperature by cooling the skin, perspiration is a natural process, necessary in maintaining optimal health. Occurring during activity or even when the body is at rest, perspiration can also be triggered by nervousness, excitement, anxiety or fear. For those involved in sports, perspiration is a common result of intense physical activity and it is safe to say that the vast majority of athletes who engage in physical sports experience some degree of perspiration during play. Interestingly, sweat itself is essentially odorless, with the odor actually caused by bacterial action that occurs after sweat is released. These bacteria are most active in moist and warm environments, particularly the armpits. For athletes who depend on heavy equipment to protect them during play, heat and moisture is trapped between the skin and the wearer's sports gear, thus resulting in excessive, noxious odors occurring.

Because equipment such as helmets, shoulder pads, elbow pads, knee pads and footwear worn by athletes such as hockey players, football players and professionals such as firemen and police officers cannot easily be laundered, these odors are easily absorbed by the equipment, resulting in the wearer encountering these stringent, intense odors each time they don their gear. Unfortunately, not only do germs and bacteria caused by perspiration result in protective gear emitting an unpleasant stench, constant exposure to these harmful agents can be unhealthy for the wearer. It is desirable that an unfavorable environment for bacteria be produced such that garments and equipment be relieved for such odors and that a freshening means be introduced to promote longevity in such items. An effective solution is necessary.

Various attempts have been made to solve problems found in sanitizer art. Among these are found in: U.S. Pat. and Pub. No. 2007/0086914 to Michael Antinozzi; U.S. Pat. No. 7,103,989 to James R. Rosseau et al; and U.S. Pat. No. 6,889,449 to Steve Silver. This prior art is representative of sanitizing means.

Ideally, a sports equipment sanitizing system, should be user-friendly and safe in-use and, yet would operate reliably and be manufactured at a modest expense. Thus, a need exists for a reliable sports equipment sanitizer system on which protective sports gear may be placed, with the unit configured to sanitize and dry the equipment between uses thus avoiding the above-mentioned problems.

BRIEF SUMMARY OF THE INVENTION

In view of the foregoing disadvantages inherent in the known sanitizing art, the present invention provides a novel sports equipment sanitizer system. The general purpose of the present invention, which will be described subsequently in greater detail, is to provide a device on which protective sports gear is placed, with the unit configured to sanitize and dry the equipment between uses. The sports equipment sanitizer may also be utilized to sanitize heavy, non-washable uniforms such as those worn by firemen and SWAT personnel. Design intent is to eliminate bacteria, germs and associated odors that have saturated athletic or professional gear via perspiration, resulting in hygienic and 'fresh' gear.

An equipment rack system is disclosed herein comprising: a plurality of holders including at least a pair of first holders, a pair of second holders, a pair of third holders, a pair of fourth holders, and a pair of fifth holders, a base; a vertical column have a first end and a second end; at least one valve; at least one hanging hook; and a powerer. The first end of the vertical column extends vertically from the base. The vertical column is approximately 3 feet in height in preferred embodiments and the equipment typically comprises sports equipment or the like. The second end of the vertical column comprises a rounded vertical support to support a helmet. Further, the second end of the vertical column comprises a cappable end. The equipment is placed on the pair of first holders, the pair of second holders, the pair of third holders, the pair of fourth holders, and the pair of fifth holders on the equipment rack during an in-use condition to sanitize and air dry equipment to neutralize odors, and eliminate bacteria, and germs. The powerer preferably operates on conventional 60 hertz, 110 volt electrical power and is connected to an electrical outlet via an elongated power cord such that the equipment rack is able to heat water to steam and to power a drying means.

The plurality of holders are each approximately 26 inches to 28 inches in total width. The pair of first holders are connected to the vertical column proximate the first end of the vertical column and the base, the pair of first holders inclined outwardly and angled upwardly from the vertical column, the pair of first holders in fluid communication with the vertical column. Each of pair of the first holders, the pair of second holders, the pair of third holders, the pair of fourth holders, and the pair of fifth holders comprise a length and a width.

The pair of first holders may be used to support a pair of shin pads. The pair of second holders are connected to the vertical column above the pair of first holders, the pair of second holders inclined outwardly and angled upwardly from the vertical column, the pair of second holders in fluid communication with the vertical column. The pair of second holders may be used to support a pair of footwear, the pair of footwear selected from the group consisting of skates, cleats, and boots. The pair of third holders are connected to the vertical column above the pair of second holders, the pair of third holders inclined outwardly and angled upwardly from the vertical column, the pair of third holders in fluid communication with the vertical column. The pair of third holders may be used to support a pair elbow pads. The pair of third holders further comprise inclined-end tips in preferred embodiments.

The pair of fourth holders are connected to the vertical column above the pair of third holders, the pair of fourth holders inclined outwardly and angled upwardly from the vertical column, the pair of fourth holders are also in fluid communication with the vertical column. Additionally, the pair of fourth holders may be used to support a pair of gloves. The pair of fourth holders comprises glove holders each preferably comprising a hand-shaped profile to rest the pair of gloves thereon. The at least one hanging hook is located directly below the pair of fourth holders, the hanging hook utilized to suspend a bucket, the bucket able to hold a plurality of hockey pucks or other small related sports accessories.

The pair of fifth holders are connected to the vertical column above the pair of fourth holders; the pair of fifth holders in fluid communication with the vertical column. The pair of fifth holders are positioned directly below the second end of the vertical column and are sculpted to provide arched ends to support shoulder pads and upper body armor. Jackets, jerseys or the like may be supported from the device using the fifth holders.

Additionally, fluid apertures are disposed along each length of each of the pair of first holders, the pair of second holders, the pair of third holders, the pair of fourth holders, and the pair of fifth holders. The vertical column also comprises the fluid apertures. The at least one fluid (air or steam) is able to pass from the base, through the vertical column and through the plurality of holders such that the at least one fluid can pass through the fluid apertures to treat equipment stored on the plurality of holders. The vertical column has an interior volume such that the at least one fluid can be passed therethrough using pressure and into the pair of first holders, the pair of second holders, the pair of third holders, the pair of fourth holders, and the pair of fifth holders such that at least one fluid can be in communication with and treat the equipment to sanitize and air dry the equipment as desired.

The valve controls a relative flow of the at least one fluid. Further, the valve permits a user to switch alternately between steam and forced air for sanitizing and drying, respectively. The valve can be manipulated to control the relative flow of the steam as the first-fluid and the relative flow of the forced air as the second-fluid suitable to treat the equipment to sanitize and air dry the equipment.

The base has an inner volume, a first inlet and a second inlet. The base comprises a reservoir for housing a sanitizing solution able to be distributed to the equipment with the steam when desired. The base may further comprise a fan motor to distribute the forced air. The first inlet permits entry of steam into the base from a steam-producing source (when not produced internally), the steam comprising the first-fluid. The second inlet permits entry of forced air into the base from an air-producing source (when not initiated internally), the forced air comprising the second-fluid.

A method of use for an equipment rack system comprises the steps of: setting equipment onto a plurality of holders (accordingly as mentioned above), the equipment to be treated; plugging in a power cord located on the equipment rack system into an electrical outlet; turning on the equipment rack system via at least one switch; treating the equipment with steam and forced air to dry; turning off the equipment rack system via the at least one switch; unplugging the power cord from the electrical outlet; and removing the equipment once treated for future use.

The present invention holds significant improvements and serves as a sports equipment sanitizer system (equipment rack system). For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, sports equipment sanitizer system (equipment rack system), constructed and operative according to the teachings of the present invention.

The various embodiments of the present invention will hereinafter be described in conjunction with the appended drawings, wherein like designations denote like elements.

DETAILED DESCRIPTION

Figure 1:
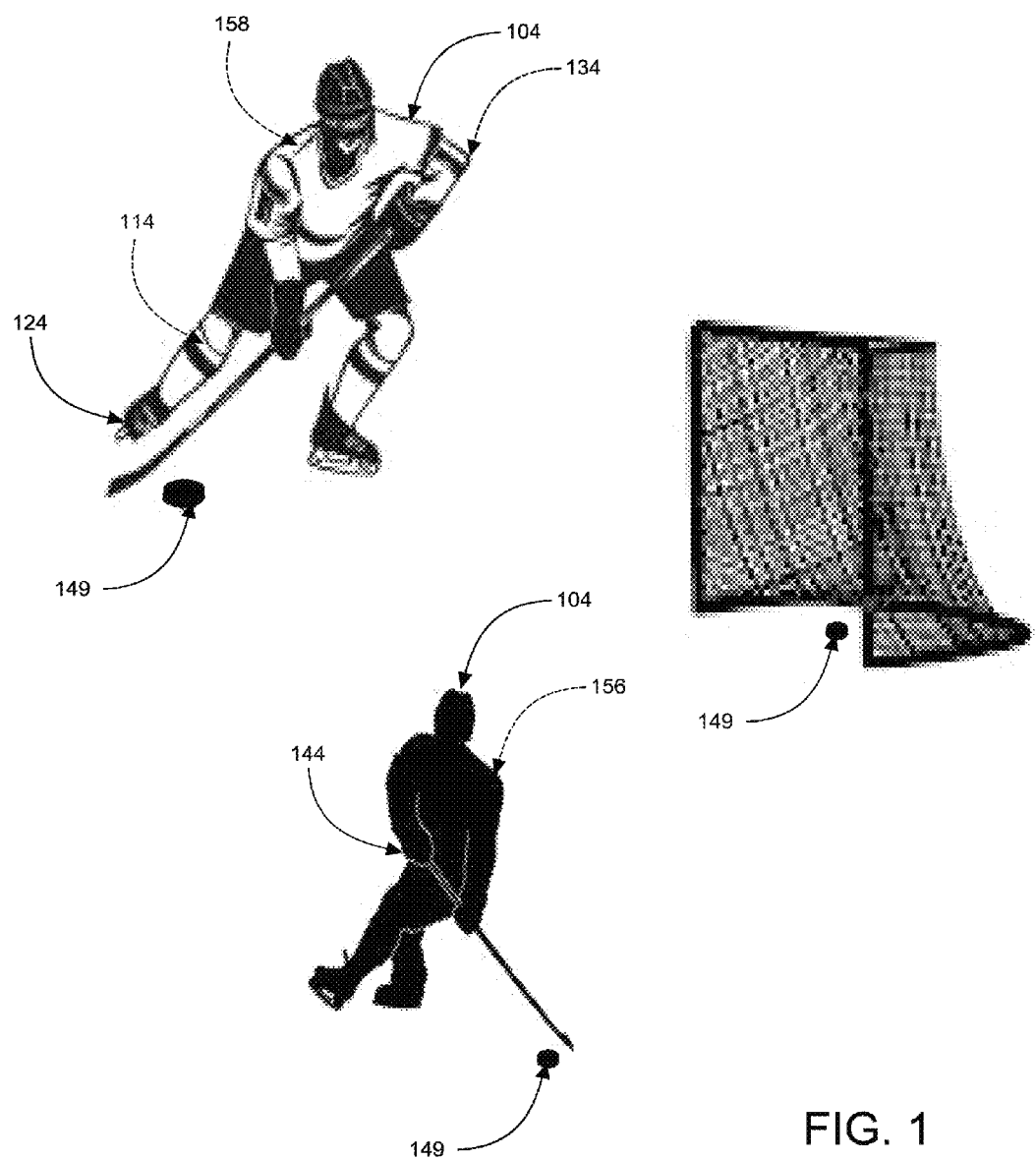
FIG. 1 shows a perspective view illustrating an equipment rack system in an in-use condition according to an embodiment of the present invention.

As discussed above, embodiments of the present invention relate to sanitizing devices and more specifically relates to a sports equipment sanitizer system (equipment rack system) where protective sports gear may be placed, with the unit configured to sanitize and dry the equipment between uses.

Generally speaking, the sports equipment sanitizer, also referred to as an equipment rack system is a specially designed mechanism, on which athletic gear and equipment such as helmets, shoulder pads, knee pads and protective pants can be hung, with the device designed expressly to sanitize and dry this gear, thus killing germs and bacteria and thwarting odors on contact, resulting in gear that is fresh and sanitary. Preferably measuring about 3 feet in total height and approximately 26 inches to 28 inches in total width, the sports equipment sanitizer is an electronic, motorized unit comprised of a base designed to rest flat on the floor, ground or other suitable surface.

Centrally positioned on this base is a vertical support post, with the top of the post featuring a rounded support that accommodates a helmet. Positioned directly below this helmet holder is a sculpted form configured expressly for holding shoulder pads or upper body armor. Generally rectangular in shape, the top of the form may be softly rounded to accommodate the curves of traditional upper body protective gear. The stand's vertical support extends from the bottom of this form to the base of the platform, with two sets of four arms extending upwards on either side of the vertical support including two sets of two arms on the front of the post and two sets of two arms on the back of the post. These support arms are preferably positioned at the midway point of the vertical support and several inches above the juncture of the post and the support stand, with the upper two front supports designed to hold gloves and the upper two rear supports designed to hold elbow pads.

The front lower supports are configured expressly to hold skates, cleats or boots, while the back lower supports are designed to hold shin pads. The upper or lower supports could also be utilized to hold protective pants or comparable gear. The most notable aspect of the sports equipment sanitizer however, is found in the internal mechanisms which serve to sanitize and dry equipment hung on the device.

The sports equipment sanitizer comprises both a sanitizer/steamer and blower-style dryer. For practical purposes, the steamer mechanism may be built into the armature of the sports equipment sanitizer and can distribute steam through a series of nozzles spaced evenly about the surface of the unit. A refillable reservoir may be incorporated into the design of the sports equipment sanitizer which could contain a sanitizing solution that kills germs and bacteria on contact, as well as neutralizes odors. This reservoir may be connected to the nozzles via a system of tubing or comparable method. As with the steamer, the dryer mechanism is able to distribute hot air through the various components of the sports equipment sanitizer by way of a series of strategically placed air vents (apertures) that are peppered about the surface of the device. The dryer's motor may be housed in the base of the unit and pushes hot air through the device when activated.

Two, push button switches are preferably located on the base of the machine to operate the sanitizer/steamer and dryer, respectively. The sports equipment sanitizer may operate on conventional 60 hertz, 110 volt electrical power and is connectable to any power outlet via an elongated power cord.

Use of the sports equipment sanitizer is relatively simple and straight forward. Athletes and/or professionals simply purchase this device as a means of carefully drying and sanitizing their equipment between uses. Once purchased, the sports equipment sanitizer may be easily installed in a designated area of the home, locker room or other appropriate location. For instance, the parents of a high school hockey star may purchase the sports equipment sanitizer to care for their son's equipment, installing the device in a household laundry room.

Alternately, a hockey coach may purchase several units for use in maintaining equipment used during practice and shared between teammates. As mentioned, the sports equipment sanitizer might also be utilized by fireman, police officers and similar professionals who depend on heavy protective gear when on the job. Use of the sports equipment sanitizer simply involves plugging the machine into any 110 wall outlet and then filling the sanitizer reservoir with a designated sanitizing and odor neutralizing solution. The user then simply places their gear over the sports equipment sanitizer as it is removed from their person. For instance, protective shoulder pads would be placed on the shoulder form, while the user's helmet would be placed on the helmet holder. Elbow pads, shin guards and skates or work boots could then be hung on the unit's individual support arms. With items loaded onto the Sports Equipment Sanitizer, the unit is then to be activated.

The user first sanitizes and steams their gear, simply by depressing the appropriate activation switch located at the base of the unit. When this occurs, a hot steam comprised of the sanitizing solution is dispersed through the device, out the apertures, directly into the interior of equipment that is hung over the unit. The sanitizing solution, in conjunction with the steam heat serves to kill germs and bacteria on contact while also neutralizing odors. Next, the user activates the unit's dryer mechanism, forcing hot air through the unit and thus quickly drying the interior of the gear that is hung over the device. With the gear properly sanitized and thoroughly dried, it may be easily removed from the sports equipment sanitizer and is ready for immediate re-use.

The sports equipment sanitizer offers consumers a number of significant benefits and advantages. Foremost, the sports equipment sanitizer provides athletes and professionals a simple and reliable way in which to sanitize and dry their protective equipment between uses. The present invention disperses a sanitizing steam over the interior of equipment hung on the device, and then dries this equipment with high powered hot air blowers, the sports equipment sanitizer effectively kills germs and bacteria that may be festering on the gear, as well as eliminates associated odors. Providing a sensible way in which to thoroughly clean equipment that cannot easily be laundered or cleaned by conventional methods, the sports equipment sanitizer is a practical product invention which results in sanitary and fresh scented equipment.

Effectively eliminating the noxious odors that can infiltrate protective hockey and other sports gear, the device would also be well suited for eradicating germs, bacteria and odors that can easily infiltrate the equipment worn by firefighters, police officers and members of the Armed Forces. Users of the device should appreciate that their gear may be easily placed on the sports equipment sanitizer as it is removed, and following steaming, sanitizing and drying, left in place atop the unit until it is needed. Sparing the user the unpleasant scenario of donning protective shoulder pads worn when playing ice hockey or other sports, only to be inundated with the noxious stench of perspiration odors, use of the sports equipment sanitizer enables athletes to dress for the big game in a more comfortable and 'fresh' fashion. Offered in a one size standard, the sports equipment sanitizer may be ideal for use in sanitizing and drying the equipment worn by children, teens and adults alike. Simple to use, consumers should appreciate the ease of which the Sports Equipment Sanitizer could be implemented. Durably constructed, the Sports Equipment Sanitizer should withstand years of repeated use, with ease.

The sports equipment sanitizer is a unique product invention that provides consumers with an easy and efficient means of eliminating odors in sporting and professional equipment. Easily operated, this sanitizer, steamer and dryer should serve a variety of useful applications.

Referring now to the drawings more specifically by numerals of reference there is shown in FIGS. 1-4, various perspective views illustrating equipment rack system 100 according to an embodiment of the present invention.

Figure 2:
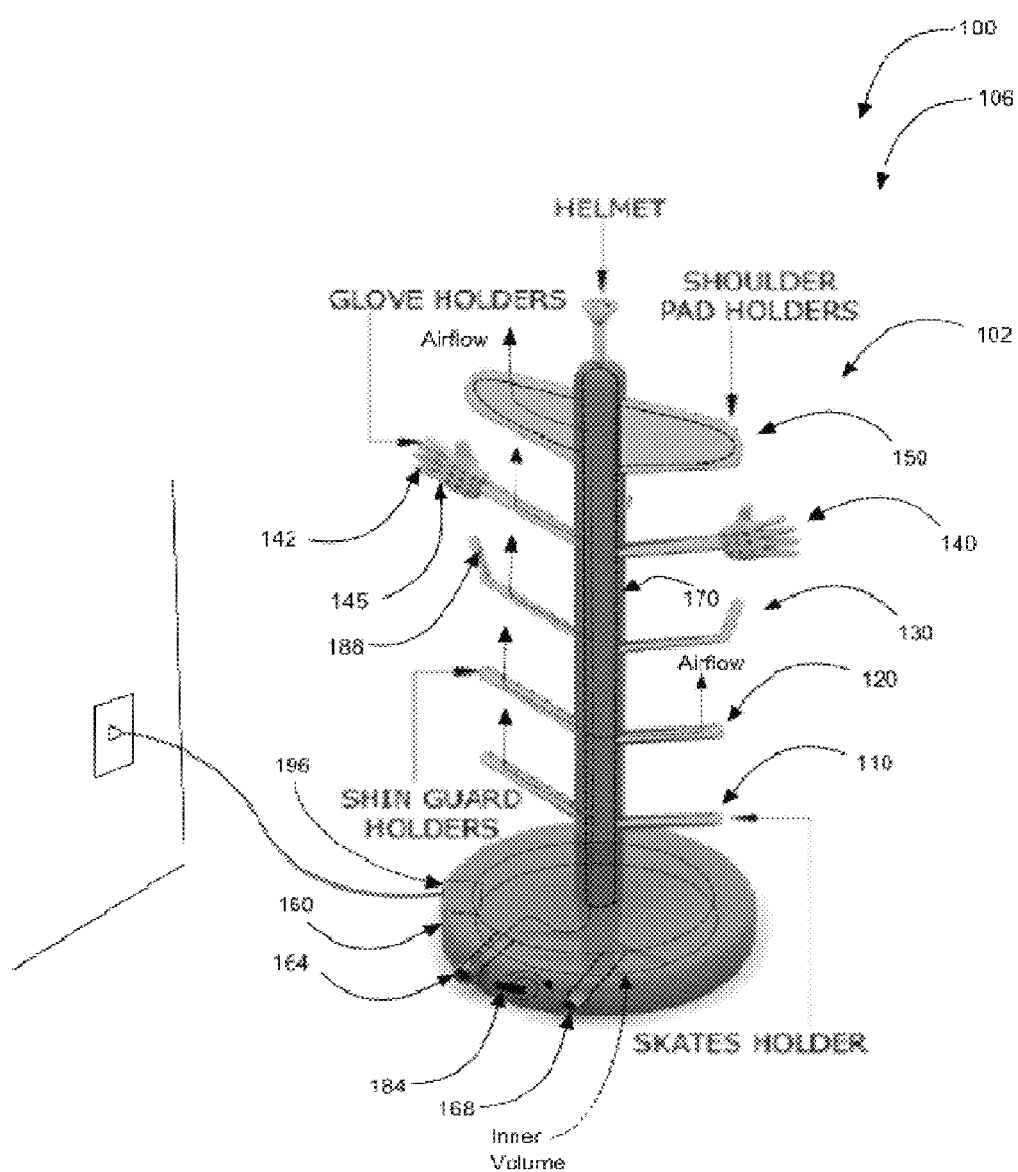
FIG. 2 is another perspective view illustrating the equipment rack system in another in-use condition according to an embodiment of the present invention of FIG. 1.
Figure 3:
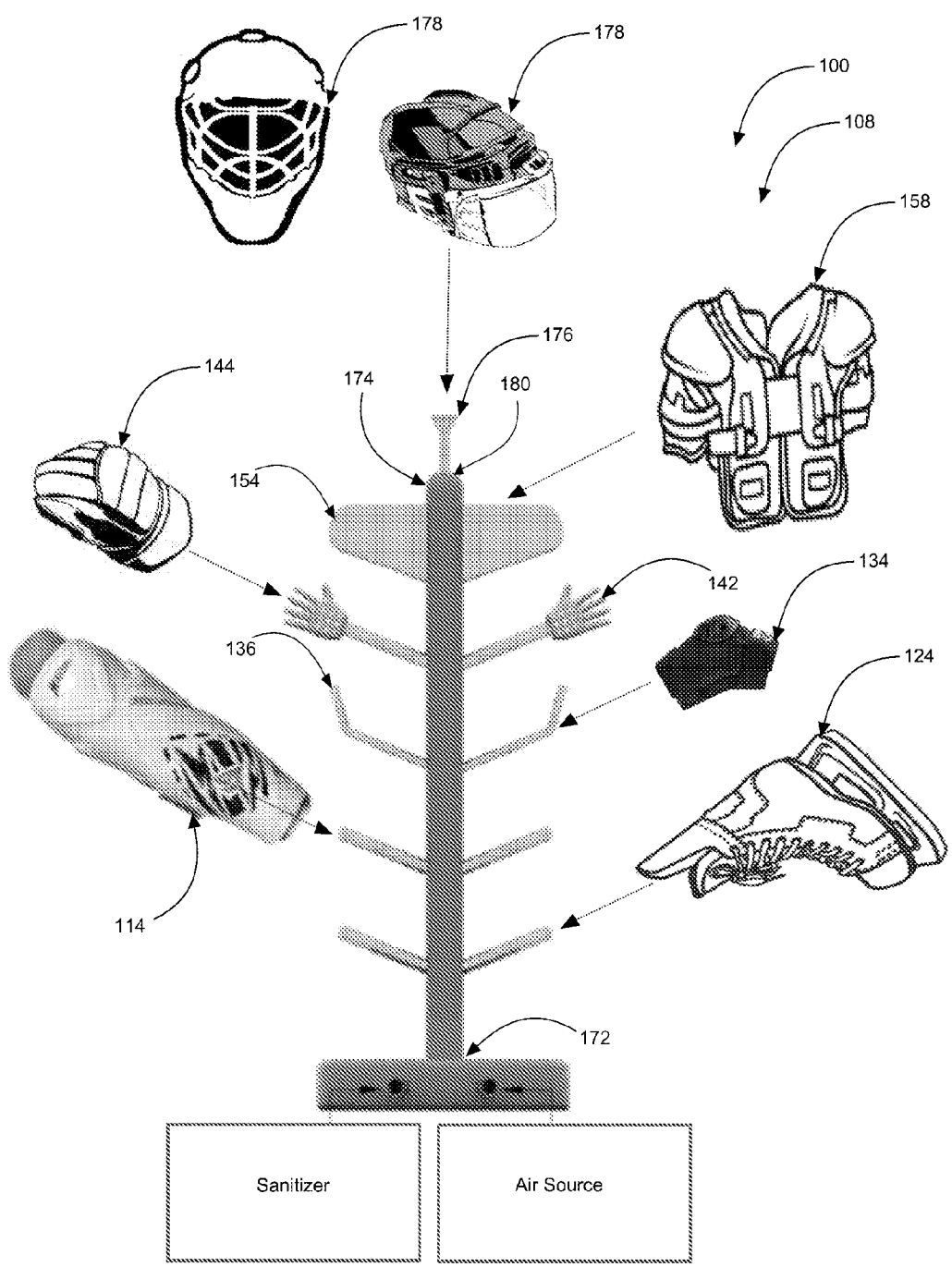
FIG. 3 is a perspective view illustrating at least one hook located on the equipment rack of the equipment rack system according to an embodiment of the present invention of FIGS. 1 and 2.
Figure 4:
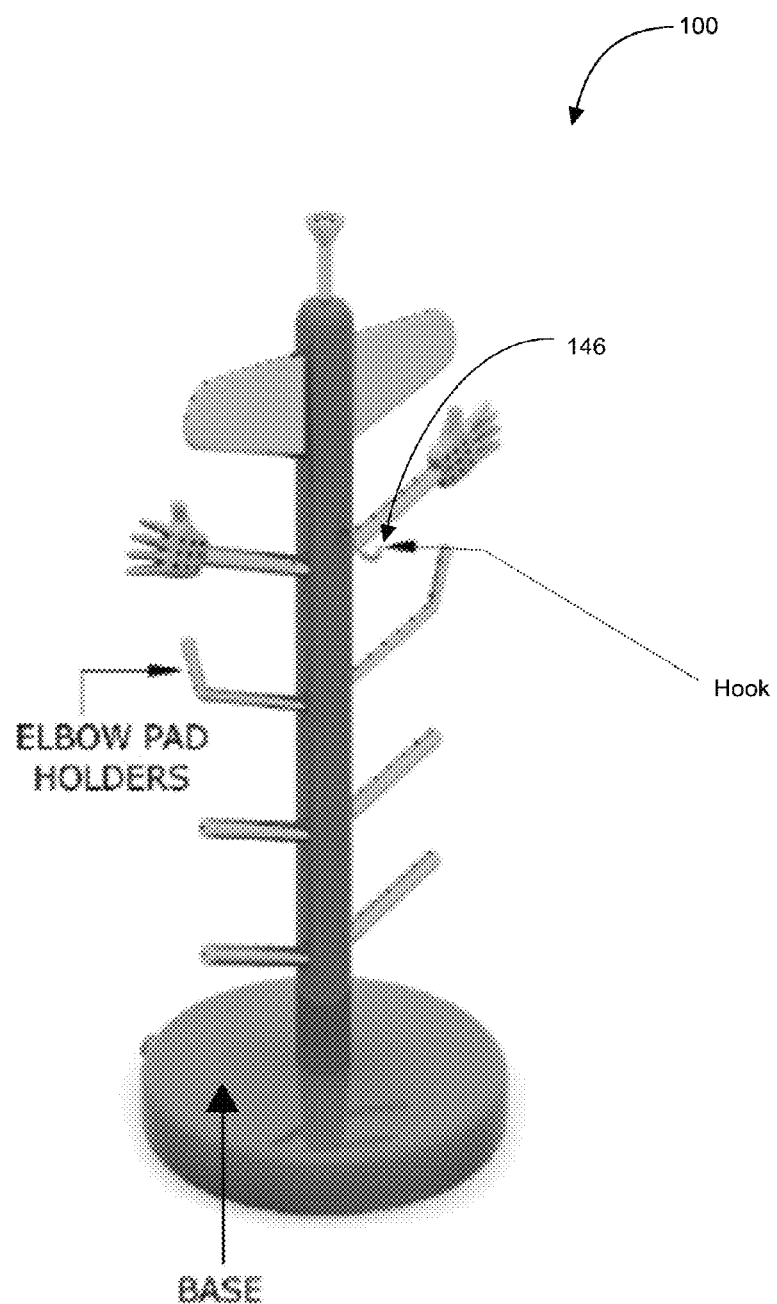
FIG. 4 is a perspective view illustrating sports equipment that is stored on equipment rack of the equipment rack system according to an embodiment of the present invention of FIGS. 1 and 2.

Equipment rack system 100 comprises: plurality of holders 102 at least including pair of first holders 110, pair of second holders 120, pair of third holders 130, pair of fourth holders 140, and pair of fifth holders 150, base 160, vertical column 170 (having first end 174 and second end 176); at least one valve 184; at least one hanging hook 146; and powerer 196 (power providing means). First end 172 of vertical column 170 preferably extends vertically from base 160. Vertical column 170 is approximately 3 feet in height in preferred embodiments and the equipment comprises sports equipment 104 as shown in FIGS. 1, 2, and 4. It should be noted that equipment rack system 100 may also be used with non-sports equipment in an alternate embodiment (not shown). The non-sports equipment is selected from the group consisting of fire-fighting-equipment, and swat-equipment. Other such equipment may be treated using the present device.

Referring now again to vertical column 170; second end 174 of vertical column 170 preferably comprises rounded vertical support 176 to support helmet 178. Further, second end 174 of vertical column 170 comprises cappable end 180. Equipment 104 is placed on pair of first holders 110, pair of second holders 120, pair of third holders 130, pair of fourth holders 140, and pair of fifth holders 150 on equipment rack 106 during in-use condition 108 to sanitize and air dry equipment 104 to neutralize odors, and eliminate bacteria, and germs. Powerer 196 operates on conventional 60 hertz, 110 volt electrical power and is connected to an electrical outlet via an elongated power cord (not shown) such that equipment rack 104 is able to heat water to steam. Powerer 196 may also be used to run fans and the like.

Plurality of holders 102 are each approximately 26 inches to 28 inches in total length. Pair of first holders 102 are connected to vertical column 170 proximate first end 172 of vertical column 170 and base 160. Pair of first holders 110 are inclined outwardly and angled upwardly from vertical column 170; pair of first holders 110 in fluid communication with vertical column 170 such that fluid communication may be achieved. Each of pair of first holders 110, pair of second holders 120, pair of third holders 130, pair of fourth holders 140, and pair of fifth holders 150 comprise a length, through which fluid (steam or air) may be communicated.

Pair of first holders 110 preferably support pair of shin pads 114. Pair of second holders 120 are connected to the vertical column 170 above pair of first holders 110, pair of second holders 120 inclined outwardly and angled upwardly from vertical column 170, pair of second holders 120 in fluid communication with vertical column 170. Pair of second holders 120 support pair of footwear 124; pair of footwear 124 selected from the group consisting of skates, cleats, and boots. Pair of third holders 130 are connected to vertical column 170 above pair of second holders 120, pair of third holders 130 inclined outwardly and angled upwardly from vertical column 170, pair of third holders 130 in fluid communication with vertical column 170. Pair of third holders 130 support pair elbow pads 134. Pair of third holders 130 further comprise inclined-end tips 136 to help equipment drip-dry quicker.

Pair of fourth holders 140 are connected to vertical column 170 above pair of third holders 130, pair of fourth holders 140 inclined outwardly and angled upwardly from vertical column 170, pair of fourth holders 140 in fluid communication with vertical column 170. Further, pair of fourth holders 140 are designed to support pair of gloves 142. Pair of fourth holders 140 comprises glove holders 144 each preferably comprising hand-shaped profile 145 to rest pair of gloves 142 thereon. At least one hanging hook 146 may be located directly below pair of fourth holders 140; hanging hook 146 utilized to suspend bucket, bucket able to hold plurality of hockey pucks 149 (or the like) as shown best in FIG. 3. Hanging hook 146 is able to hold hockey pants or the like (not shown).

Pair of fifth holders 150 are connected to vertical column 170 above pair of fourth holders 140; pair of fifth holders 150 in fluid communication with vertical column 170. Pair of fifth holders 150 are preferably positioned directly below second end 174 of vertical column 170 and are sculpted to provide arched ends 154 to support shoulder pads 156 and upper body armor 158. Jerseys, jackets and other such garments may be held by fifth holders 150.

Additionally, fluid apertures 188 are disposed along each length of each of pair of first holders 110, pair of second holders 120, pair of third holders 130, pair of fourth holders 140, and pair of fifth holders 150. Vertical column 170 also comprises fluid apertures 188. At least one fluid is able to pass from base 160, through vertical column 170 and through plurality of holders 102 such that the at least one fluid can pass through and out of fluid apertures 188 to treat equipment 104 stored on plurality of holders 102. Vertical column 170 has an interior volume (not shown) such that the at least one fluid can be passed therethrough preferably using pressure and into pair of first holders 110, pair of second holders 120, pair of third holders 130, pair of fourth holders 140, and pair of fifth holders 150 such that at least one fluid can be in communication with and treat equipment 104 to sanitize and air dry equipment 104. The various parts are hollow such that water, steam and air can be passed therethrough.

Valve 184 may be used to control a relative flow of the at least one fluid. Further, valve 184 permits a user to switch alternately between steam and forced air for sanitizing and drying, respectively. Valve 184 can be manipulated to control the relative flow of the steam as the first-fluid and the relative flow of the forced air as the second-fluid suitable to treat the equipment to sanitize and air dry equipment 104.

Base 160 has an inner volume, first inlet 164, and second inlet 168. Base 160 in certain embodiments may comprise a reservoir for housing a sanitizing solution able to be distributed to equipment 104 with the steam. Base 160 may also further comprise a fan motor to distribute the forced air. In other embodiments first inlet 164 permits entry of steam into base 160 from a steam-producing source, the steam comprising a first-fluid. Second inlet 168 permits entry of forced air into base 160 from an air-producing source, the forced air comprising a second-fluid. The present invention is thus able to be remotely provided with steam and/or forced air via first inlet 164 and second inlet 168 for example if a plurality of the devices are lined up in a locker room for use by a team.

Figure 5:
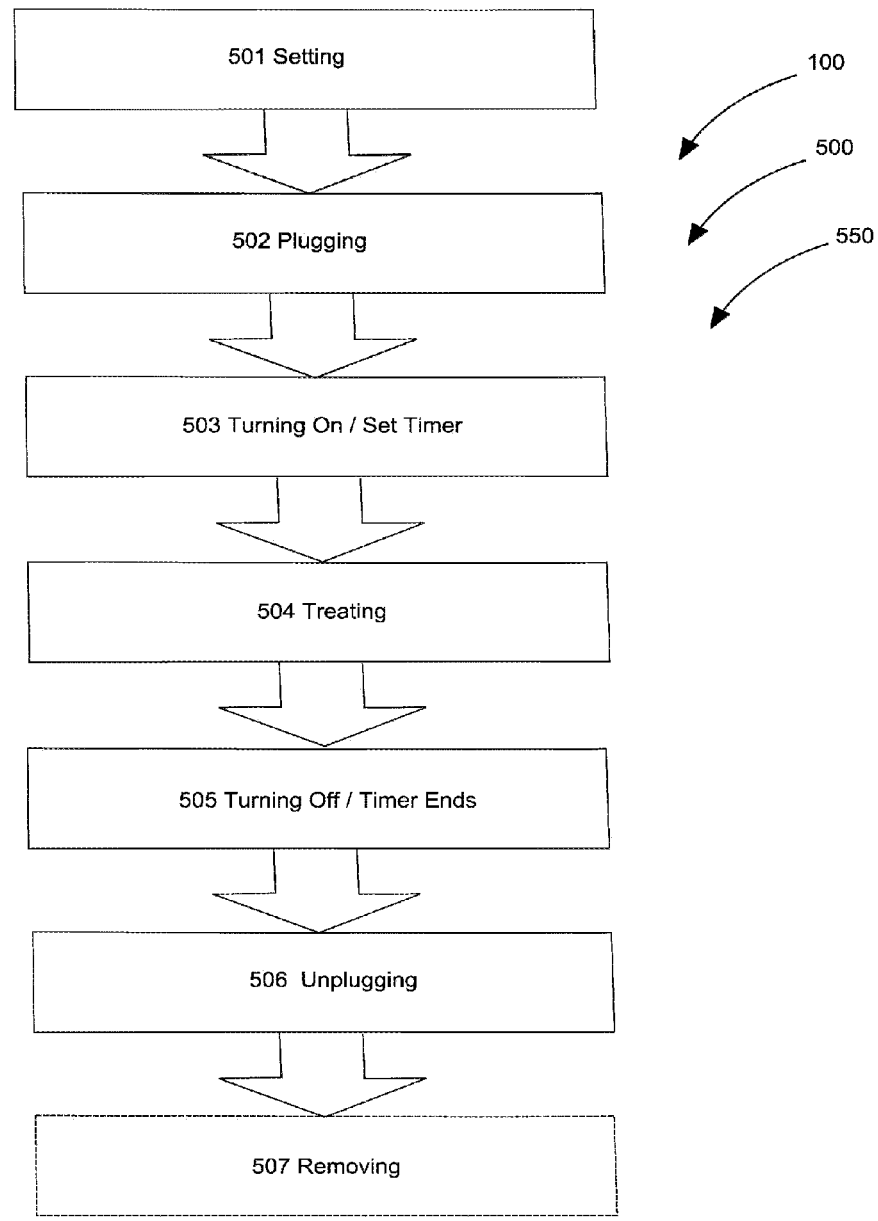
FIG. 5 is a flowchart illustrating a method of use for the equipment rack system according to an embodiment of the present invention of FIGS. 1-4.

Referring now to FIG. 5, flowchart 550 illustrating method of use 500 for equipment rack system 100 according to an embodiment of the present invention of FIGS. 1-4.

Method of use 500 for equipment rack system 100 preferably comprises the steps of: step one 501 setting (placing) equipment 104 onto plurality of holders 102, equipment 104 to be treated; step two 502 plugging in a power cord located on equipment rack system 100 into an electrical outlet; step three 503 turning on (setting a timer for) equipment rack system 100 via at least one switch; step four 504 treating equipment 104 with steam to sanitize and forced air to dry (respectively); step five 505 turning off (timer ending) equipment rack system 100 via at least one switch; step six 506 unplugging the power cord from the electrical outlet; and step seven 507 removing equipment 104 once treated for future use.

It should be noted that the steps described in the method of use can be carried out in many different orders according to user preference. The use of "step of" should not be interpreted as "step for", in the claims herein and is not intended to invoke the provisions of 35 U.S.C. §112, ¶ 6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. An equipment rack system comprising:
   a plurality of holders at least including;
      a pair of first holders;
      a pair of second holders;
      a pair of third holders;
      a pair of fourth holders; and
      a pair of fifth holders;
   a base;
   a vertical column have a first end and a second end; and
   at least one valve; and
   wherein said first end of said vertical column extends vertically from said base;
   wherein said second end of said vertical column comprises a cappable end;
   wherein said pair of first holders are connected to said vertical column proximate said first end of said vertical column and said base, said pair of first holders inclined outwardly and angled upwardly from said vertical column, said pair of first holders in fluid communication with said vertical column;
   wherein said pair of second holders are connected to said vertical column above said pair of first holders, said pair of second holders inclined outwardly and angled upwardly from said vertical column, said pair of second holders in fluid communication with said vertical column;
   wherein said pair of third holders are connected to said vertical column above said pair of second holders, said pair of third holders inclined outwardly and angled upwardly from said vertical column, said pair of third holders in fluid communication with said vertical column;
   wherein said pair of fourth holders are connected to said vertical column above said pair of third holders, said pair of fourth holders inclined outwardly and angled upwardly from said vertical column, said pair of fourth holders in fluid communication with said vertical column;
   wherein said pair of fifth holders are connected to said vertical column above said pair of fourth holders, said pair of fifth holders in fluid communication with said vertical column;
   wherein each of said pair of first holders, said pair of second holders, said pair of third holders, said pair of fourth holders, and said pair of fifth holders comprise a length;
   wherein fluid apertures are disposed along each said length of each of said pair of first holders, said pair of second holders, said pair of third holders, said pair of fourth holders, and said pair of fifth holders;
   wherein said vertical column comprises said fluid apertures;
   wherein at least one fluid is able to pass from said base, through said vertical column and through said plurality of holders such that said at least one fluid can pass through said fluid apertures to treat equipment stored on said plurality of holders;
   wherein said valve controls a relative flow of said at least one fluid;
   wherein said base has an inner volume, a first inlet and a second inlet;
   wherein said vertical column has an interior volume such that said at least one fluid can be passed therethrough using pressure and into said pair of first holders, said pair of second holders, said pair of third holders, said pair of fourth holders, and said pair of fifth holders such that said at least one fluid can be in communication with and treat said equipment to sanitize and air dry said equipment;
   wherein said first inlet permits entry of steam into said base from a steam-producing source, said steam comprising a first-fluid;
   wherein said second inlet permits entry of forced air into said base from an air-producing source, said forced air comprising a second-fluid;
   wherein said valve can be manipulated to control said relative flow of said steam as said first-fluid and said relative flow of said forced air as said second-fluid suitable to treat said equipment to sanitize and air dry said equipment, respectively; and
   wherein said equipment is placed on said pair of first holders, said pair of second holders, said pair of third holders, said pair of fourth holders, and said pair of fifth holders on said equipment rack during an in-use condition to sanitize and air dry said equipment to neutralize odors, and eliminate bacteria, and germs.

2. The equipment rack system of claim 1 wherein said vertical column is approximately 3 feet in height and said equipment comprises sports equipment.

3. The equipment rack system of claim 1 wherein said plurality of holders are each approximately 26 inches to 28 inches in total width.

4. The equipment rack of claim 1 wherein said second end of said vertical column comprises a rounded vertical support to support a helmet.

5. The equipment rack of claim 1 wherein said pair of fifth holders are positioned directly below said second end of said vertical column and are sculpted to provide arched ends to support shoulder pads and upper body armor.

6. The equipment rack of claim 1 wherein said pair of fourth holders support a pair of gloves.

7. The equipment rack of claim 1 wherein said pair of third holders support a pair elbow pads.

8. The equipment rack of claim 1 wherein said pair of second holders support a pair of footwear, said pair of footwear selected from the group consisting of skates, cleats, and boots.

9. The equipment rack of claim 1 wherein said pair of first holders support a pair of shin pads.

10. The equipment rack of claim 1 further comprising at least one hanging hook located directly below said pair of fourth holders, said hanging hook utilized to suspend a bucket, said bucket able to hold a plurality of hockey pucks.

11. The equipment rack of claim 6 wherein said pair of fourth holders comprises glove holders each comprising a hand-shaped profile to rest said pair of gloves thereon.

12. The equipment rack of claim 1 wherein said pair of third holders further comprise inclined-end tips.

13. The equipment rack of claim 1 wherein said base comprises a reservoir for housing a sanitizing solution able to be distributed to said equipment with said steam.

14. The equipment rack of claim 1 wherein said base further comprises a fan motor to distribute said forced air.

15. The equipment rack of claim 1 wherein said valve permits a user to switch alternately between said steam and said forced air for sanitizing and drying, respectively.

16. The equipment rack of claim 1 further comprising a powerer which operates on conventional 60 hertz, 110 volt electrical power and is connected to an electrical outlet via an elongated power cord such that said equipment rack is able to heat water to said steam.

17. The equipment rack of claim 1 wherein said equipment comprises non-sports equipment.

18. The equipment rack system of claim 17 wherein said non-sports equipment is selected from the group consisting of fire-fighting-equipment, and swat-equipment.

19. An equipment rack system comprising:
a plurality of holders at least including;
a pair of first holders;
a pair of second holders;
a pair of third holders;
a pair of fourth holders; and
a pair of fifth holders;
a base;
a vertical column have a first end and a second end;
at least one valve;
at least one hanging hook; and
a powerer;
wherein said first end of said vertical column extends vertically from said base;
wherein said vertical column is approximately 3 feet in height and equipment supported on said plurality of holders comprises sports equipment;
wherein said second end of said vertical column comprises a rounded vertical support to support a helmet;
wherein said second end of said vertical column comprises a cappable end;
wherein said plurality of holders are each approximately 26 inches to 28 inches in total width;
wherein said pair of first holders are connected to said vertical column proximate said first end of said vertical column and said base, said pair of first holders inclined outwardly and angled upwardly from said vertical column, said pair of first holders in fluid communication with said vertical column;
wherein said pair of first holders support a pair of shin pads;
wherein said pair of second holders are connected to said vertical column above said pair of first holders, said pair of second holders inclined outwardly and angled upwardly from said vertical column, said pair of second holders in fluid communication with said vertical column;
wherein said pair of second holders support a pair of footwear;
wherein said pair of third holders are connected to said vertical column above said pair of second holders, said pair of third holders inclined outwardly and angled upwardly from said vertical column, said pair of third holders in fluid communication with said vertical column;
wherein said pair of third holders support a pair elbow pads;
wherein said pair of third holders further comprise inclined-end tips;
wherein said pair of fourth holders are connected to said vertical column above said pair of third holders, said pair of fourth holders inclined outwardly and angled upwardly from said vertical column, said pair of fourth holders in fluid communication with said vertical column;
wherein said pair of fourth holders support a pair of gloves;
wherein said pair of fourth holders comprises glove holders each comprising a hand-shaped profile to rest said pair of gloves thereon;
wherein at least one hanging hook is located directly below said pair of fourth holders, said hanging hook utilized to suspend a bucket, said bucket able to hold a plurality of hockey pucks;
wherein said pair of fifth holders are connected to said vertical column above said pair of fourth holders, said pair of fifth holders in fluid communication with said vertical column;
wherein said pair of fifth holders are positioned directly below said second end of said vertical column and are sculpted to provide arched ends and a flat-top to support shoulder pads and upper body armor;
wherein each of said pair of first holders, said pair of second holders, said pair of third holders, said pair of fourth holders, and said pair of fifth holders comprise a length;
wherein fluid apertures are disposed along each said length of each of said pair of first holders, said pair of second holders, said pair of third holders, said pair of fourth holders, and said pair of fifth holders;
wherein said vertical column comprises said fluid apertures;
wherein at least one fluid is able to pass from said base, through said vertical column and through said plurality of holders such that said at least one fluid can pass through said fluid apertures to treat equipment stored on said plurality of holders;
wherein said valve controls a relative flow of said at least one fluid;
wherein said valve permits a user to switch alternately between steam and forced air for sanitizing and drying, respectively;
wherein said base has an inner volume, a first inlet and a second inlet;
wherein said base comprises a reservoir for housing a sanitizing solution able to be distributed to said equipment with said steam;
wherein said base further comprises a fan motor to distribute said forced air;
wherein said vertical column has an interior volume such that said at least one fluid can be passed therethrough using pressure and into said pair of first holders, said pair of second holders, said pair of third holders, said pair of fourth holders, and said pair of fifth holders such that said at least one fluid can be in communication with and treat said equipment to sanitize and air dry said equipment;
wherein said first inlet permits entry of water to be made into said steam into said base, said steam comprising a first-fluid;
wherein said second inlet permits entry of forced air into said base from an air-producing source, said forced air comprising a second-fluid;
wherein said powerer operates on conventional 60 hertz, 110 volt electrical power and is connected to an electrical outlet via an elongated power cord such that said equipment rack is able to heat water to said steam;

wherein said valve can be manipulated to control said relative flow of said steam as said first-fluid and said relative flow of said forced air as said second-fluid suitable to treat said equipment to sanitize and air dry said equipment, respectively; and wherein said equipment is placed on said pair of first holders, said pair of second holders, said pair of third holders, said pair of fourth holders, and said pair of fifth holders on said equipment rack during an in-use condition to sanitize and air dry said equipment to neutralize odors, and eliminate bacteria, and germs.

20. A method of using an equipment rack system comprising the steps of:

setting equipment onto a plurality of holders, said equipment to be treated;

plugging in a power cord located on said equipment rack system into an electrical outlet;

turning on said equipment rack system via at least one switch;

treating said equipment with steam to sanitize and forced air to dry;

turning off said equipment rack system via said at least one switch;

unplugging said power cord from said electrical outlet; and removing said equipment once treated for future use.

* * * * *